(12) United States Patent
Bortkiewicz

(10) Patent No.: US 7,182,762 B2
(45) Date of Patent: Feb. 27, 2007

(54) ELECTROSURGICAL DEVICE

(75) Inventor: Andzrej Bortkiewicz, South Hamilton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 201 days.

(21) Appl. No.: 10/747,101

(22) Filed: Dec. 30, 2003

(65) Prior Publication Data

US 2005/0143726 A1    Jun. 30, 2005

(51) Int. Cl.
*A61B 18/14*    (2006.01)
(52) U.S. Cl. .............................. 606/41; 606/45; 606/49
(58) Field of Classification Search .................. 606/41, 606/45, 49
See application file for complete search history.

(56) References Cited

U.S. PATENT DOCUMENTS

| | | | |
|---|---|---|---|
| 164,184 A | 6/1875 | Kidder | |
| 3,460,539 A | 8/1969 | Anhalt, Sr. | |
| 3,920,021 A | 11/1975 | Hiltebrandt | |
| 4,033,351 A | 7/1977 | Hetzel | |
| 4,232,676 A | * 11/1980 | Herczog | 606/50 |
| 4,654,024 A | 3/1987 | Crittenden et al. | |
| 4,765,331 A | 8/1988 | Petruzzi et al. | |
| 4,799,480 A | 1/1989 | Abraham et al. | |
| 4,832,048 A | 5/1989 | Cohen | |
| 5,057,106 A | 10/1991 | Kasevich et al. | |
| 5,380,320 A | * 1/1995 | Morris | 606/45 |
| 5,383,917 A | 1/1995 | Desai et al. | |
| 5,419,767 A | 5/1995 | Eggers et al. | |
| 5,454,809 A | 10/1995 | Janssen | |
| 5,562,720 A | 10/1996 | Stern et al. | |
| 5,643,197 A | 7/1997 | Brucker et al. | |
| 5,681,282 A | 10/1997 | Eggers et al. | |
| 5,683,366 A | 11/1997 | Eggers et al. | |
| 5,697,536 A | 12/1997 | Eggers et al. | |
| 5,766,153 A | 6/1998 | Eggers et al. | |

(Continued)

FOREIGN PATENT DOCUMENTS

| | | |
|---|---|---|
| WO | WO 96/10367 | 4/1996 |
| WO | WO 00/53113 | 9/2000 |

OTHER PUBLICATIONS

Laroussi, Mounir, "Nonthermal Decontamination of Biological Media by Atmospheric-Pressure Plasmas: Review, Analysis, and Prospects" IEE Transactions on Plasma Science, vol. 30, No. 4, Aug. 2002.

(Continued)

*Primary Examiner*—Lee S. Cohen
(74) *Attorney, Agent, or Firm*—Fish & Richardson P.C.

(57) ABSTRACT

An electrosurgical device includes a high dielectric material and at least one conductor arranged relative to the high dielectric material such that, in use, the high dielectric material is disposed between the conductor and target tissue. A second conductor is arranged relative to the high dielectric material such that, in use, the high dielectric material is disposed between the second conductor and target tissue. Each conductor includes a plurality of conductive fingers interleaved, e.g. in a comb-like fashion or as concentric circles. A method for performing electrosurgery includes delivering energy to a target tissue through a high dielectric material. The electrosurgery includes, e.g., ablation, coagulation, or the treatment of skin lesions.

40 Claims, 10 Drawing Sheets

U.S. PATENT DOCUMENTS

| | | |
|---|---|---|
| 5,769,879 A | 6/1998 | Richards et al. |
| 5,843,075 A | 12/1998 | Taylor |
| 5,860,951 A | 1/1999 | Eggers et al. |
| 5,871,469 A | 2/1999 | Eggers et al. |
| 6,068,628 A | 5/2000 | Fanton et al. |
| 6,179,836 B1 | 1/2001 | Eggers et al. |
| 6,190,382 B1 | 2/2001 | Ormsby et al. |
| 6,264,650 B1 | 7/2001 | Hovda et al. |
| 6,312,408 B1 | 11/2001 | Eggers et al. |
| 6,413,255 B1 * | 7/2002 | Stern .................... 606/41 |
| 6,416,507 B1 | 7/2002 | Eggers et al. |
| 6,692,489 B1 | 2/2004 | Heim et al. |
| 6,758,846 B2 * | 7/2004 | Goble et al. ............ 606/41 |
| 2003/0216728 A1 | 11/2003 | Stern et al. |
| 2003/0220635 A1 | 11/2003 | Knowlton et al. |

OTHER PUBLICATIONS

International Search Report dated Apr. 13, 2005 for International Application No. PCT/US2004/043110.

Written Opinion dated Apr. 13, 2005 for International Application No. PCT/US2004/043110.

Tasto et al., Radiofrequency Microdebridement: A Novel Treatment Option for Tendinopathies, available at http://www.topazinfo.com/intl/physician/clinicals/whitepaper.htm, available as of Feb. 12, 2003 according to www.archive.org.

* cited by examiner

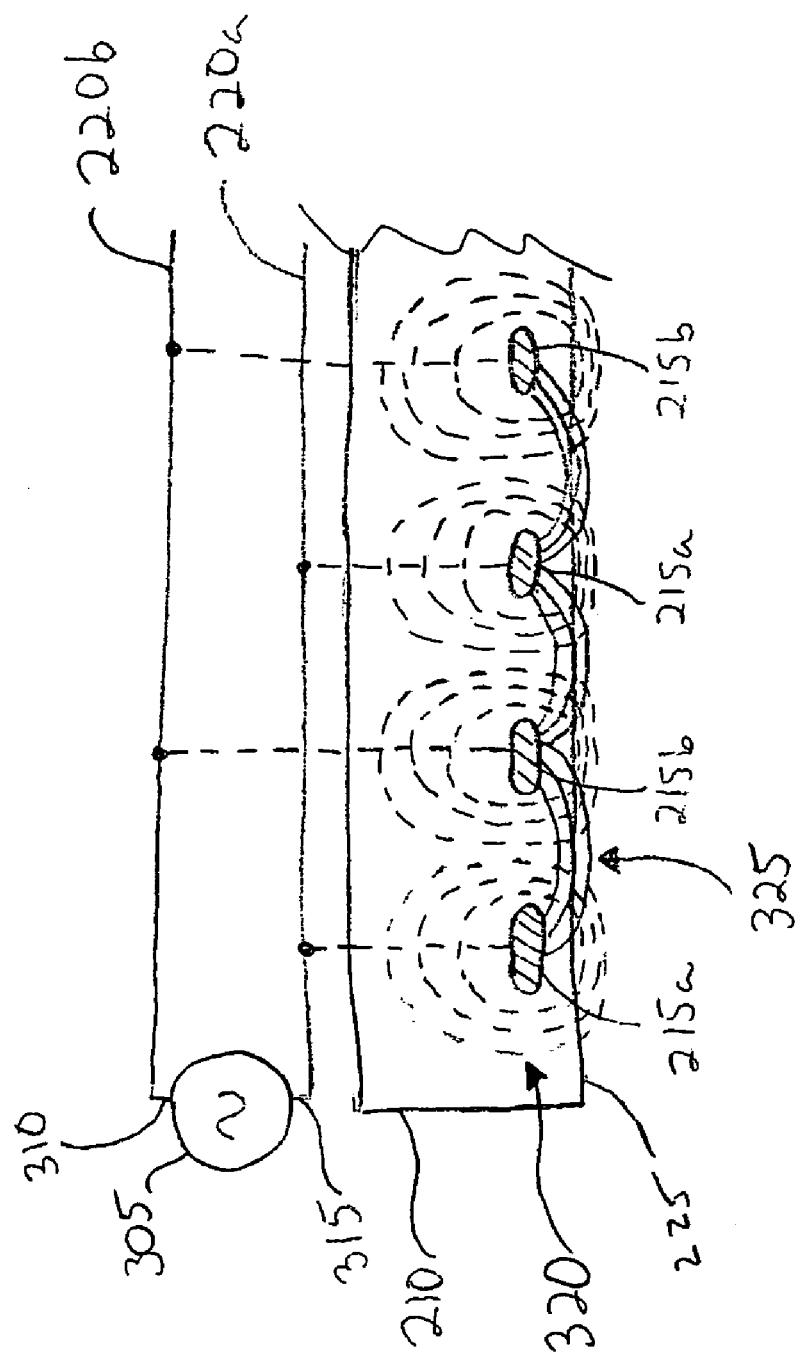

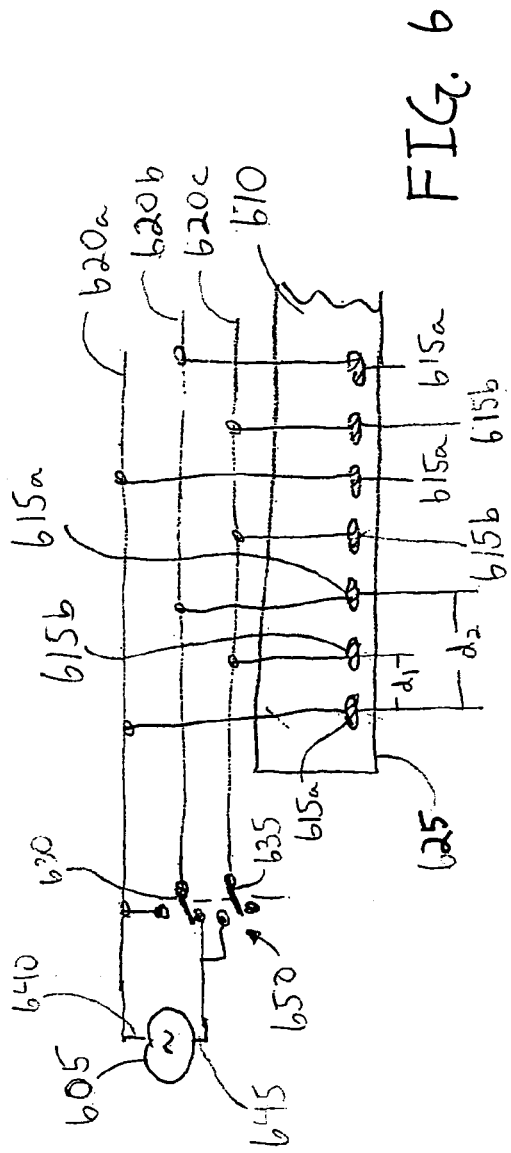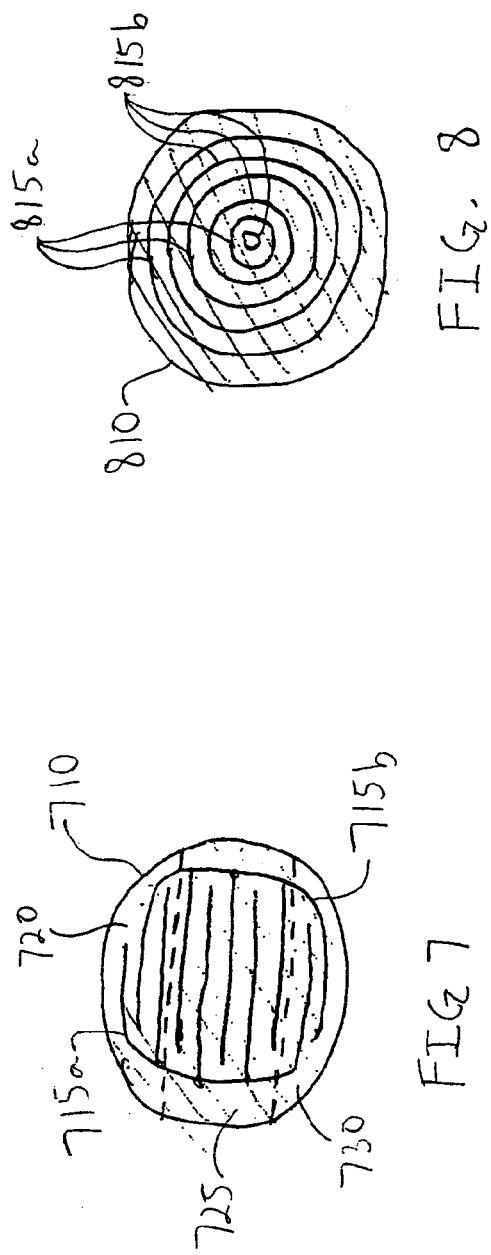

ELECTROSURGICAL DEVICE

TECHNICAL FIELD

This description is related to surgical devices and methods for applying thermal and/or electrical energy to organic material such as biological tissue to modify characteristics of the tissue for therapeutic purposes. More particularly, the description is related to electrosurgical devices using radio frequency (RF) energy to cut, coagulate, ablate, or otherwise treat tissue during a medical procedure.

BACKGROUND

Surgical instruments employing RF energy for treatment are used in a variety of surgical procedures. Such instruments generally include an RF probe that delivers RF energy to the part of the body to be affected by the electrosurgical procedure.

Present RF probes are typically either mono-polar or bi-polar probes. Mono-polar probes have a single RF electrode. The RF energy of the mono-polar probe passes from the RF electrode through the area to be treated and then returns through a return electrode attached to the body, often a foot or more away. Bipolar probes include two terminals, an active electrode and a return electrode, which are both positioned within the patient at the area to be treated.

SUMMARY

In one aspect, an electrosurgical device includes a high dielectric material and at least one conductor arranged relative to the high dielectric material such that, in use, the high dielectric material is disposed between the conductor and target tissue.

Implementations of this aspect may include one or more of the following features. A second conductor is arranged relative to the high dielectric material such that, in use, the high dielectric material is disposed between the second conductor and target tissue. Each conductor includes a plurality of conductive fingers. The first plurality of fingers is interleaved, e.g. in a comb-like fashion, with the second plurality of fingers. The device includes a RF power generator and a network coupling the first and second plurality of fingers to the RF power generator.

In an illustrated embodiment, a switching network coupling the RF generator to the conductive fingers controls the depth of treatment of the tissue. The switching network has a first state in which an RF electrical field extends to a first length from a tissue treatment surface of the high dielectric material and a second state in which the RF electrical field extends to a second length from the tissue treatment surface, which is longer than the first length.

In another embodiment, each of the conductors includes a set of concentric circles, and the concentric circles are interleaved.

The RF power generator connected to the conductor is configured to provide RF power with a voltage and a frequency sufficient to produce a dielectric barrier discharge plasma at the surface of the high dielectric material. The RF generator is configured to provide RF power at a frequency up to about 20 MHz and a voltage up to about 1500 Vrms. The RF generator is configured to provide RF power with a voltage and a frequency sufficient to result in a current density at a surface of the high dielectric material that is greater than about 0.2 amperes per millimeter squared and that can be as high as about 1.0 ampere per millimeter squared.

The high dielectric material includes a ceramic material. The high dielectric material is a material having a dielectric constant greater than approximately 10, e.g., typically between about 100 and 1000.

In another aspect, a method for performing electrosurgery includes delivering energy to a target tissue through a high dielectric material.

Implementations of this aspect may include one or more of the following features.

The electrosurgery includes ablating or coagulating the target tissue or treating lesions. Delivering the energy includes forming a dielectric barrier discharge plasma; high density RF currents (for thermal treatment); or a high strength RF electrical field (for voltage treatment) at the surface of the high dielectric material. Energy is delivered with a frequency up to about 20 MHz and a RF power density up to about 50 W per millimeter squared.

The target tissue is in either a non-conductive or conductive environment. The target tissue can be a variety of biological tissues such as, e.g., cartilage, muscle, fat, or ligament.

In another aspect, an electrosurgical device includes a high dielectric material and at least one conductor arranged relative to the high dielectric material such that, in use, energy is delivered to a target tissue through the high dielectric material.

In another aspect, RF energy is applied to a target tissue with a conductor without galvanic contact between the conductor and the target tissue or between the conductor and a conductive medium surrounding the target tissue.

In another aspect, an electrosurgical device includes means for providing electrical energy and means for distributing the electrical energy so as to obtain a substantially uniform field distribution, wherein, in use, the substantially uniform field distribution is applied to a target tissue.

In another aspect, an electrosurgical device includes means for providing electrical energy and means for applying the electrical energy to a target tissue such that electric current does not flow through tissue immediately adjacent to the target tissue.

Advantages may include one or more of the following. For example, the present device and method eliminates or reduces the RF return current and high electrical field present in the tissue surrounding the targeted tissue, thereby reducing or eliminating collateral damage. The configuration of the device provides for a stable discharge region that can be ignited regardless of the device's proximity to tissue and with properties that are not dependent on the device's proximity to tissue. The RF energy is distributed evenly due to impedance of the ceramic. The RF energy is concentrated in a very thin layer at the surface of the ceramic. There is no return path of RF current in the tissue. The ceramic prevents concentration of the RF energy in a small region of the treated area.

The apparatus and method are applicable in a wide variety of medical procedures on a wide range of different bodily tissues. The apparatus can be used in electrosurgery in a saline environment or in glycine or air and can be used, e.g., to treat chondromalacia and for surgery on anterior cruciate ligaments.

The details of one or more implementations are set forth in the accompanying drawings and the description below. Other features, objects, and advantages will be apparent from the description and drawings, and from the claims.

DESCRIPTION OF DRAWINGS

FIG. 3 is a schematic diagram showing the connection of electrical energy to the electrosurgical device.

FIG. 6 is a schematic diagram showing a switching network for use with the electrosurgical device.

FIGS. 7 and 8 are plan views showing alternate configuration for the distal portion.

DETAILED DESCRIPTION

Figure 1:
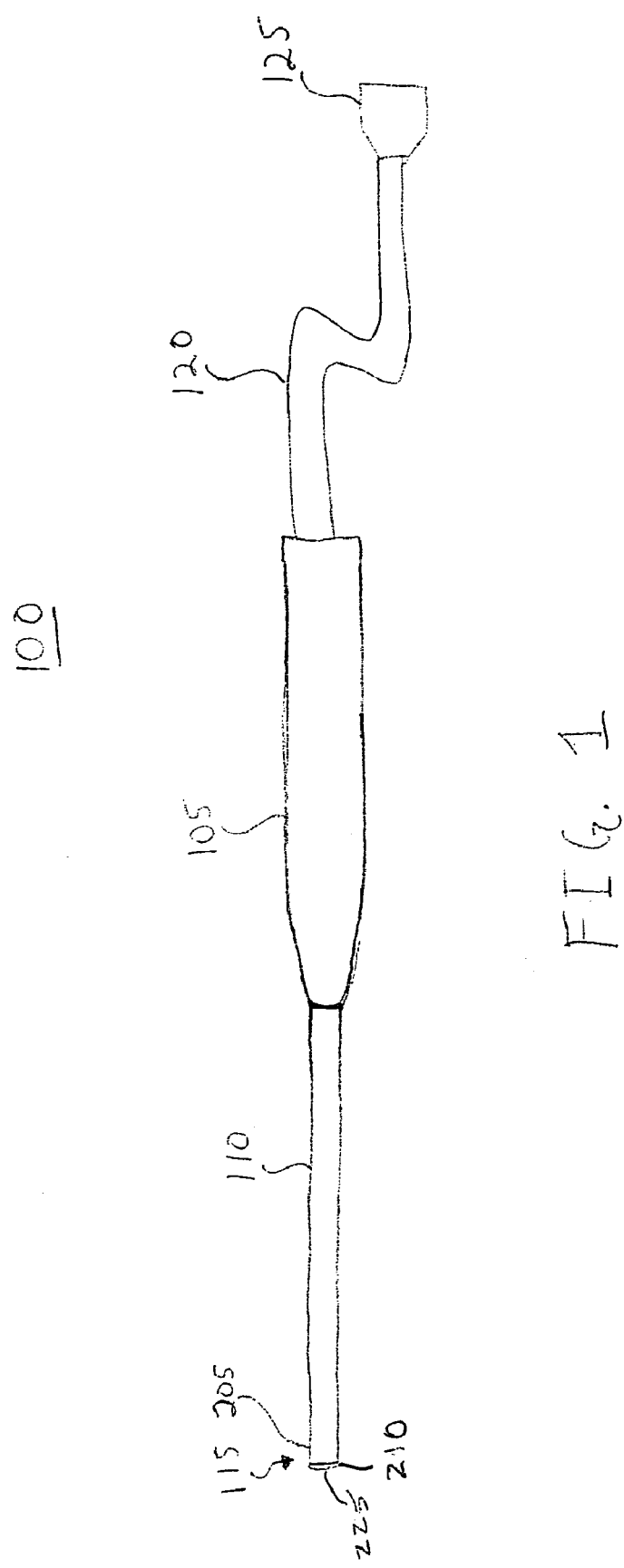
FIG. 1 is a side view of an electrosurgical device.

Referring to FIG. 1, an electrosurgical device 100 includes a handle 105 connected to an elongated shaft 110 and a power cable 120. Power cable 120 includes a power connector 125 for connection to a source of electrical energy such as an RF power generator (not shown). Shaft 110 is hollow and formed from, e.g., an insulative plastic such as Teflon, polyethylene, polystyrene, or other thermally molded plastic, or made from a metal tube.

Shaft 110 has a distal portion 115 that includes an insulated region 205 terminating at a disc 210. Disc 210 is, e.g., approximately 5 mm in diameter and has an overall thickness of between 25 and 60 mils. Disc 210 has a tissue treatment surface 225 and is formed of a high dielectric material, that is, a material having a dielectric constant greater than about 10, preferably between 100 and 1000.

Figure 2B:
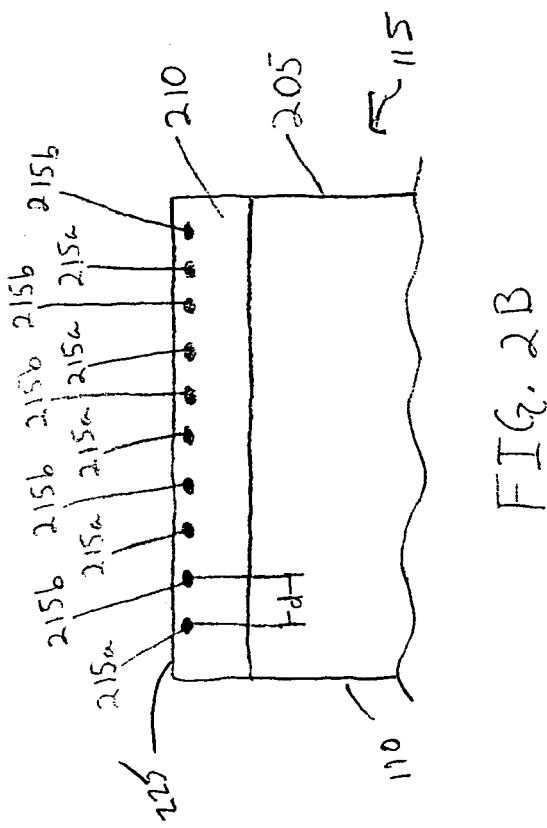
FIG. 2B is a cross-sectional view of the distal portion of the device taken along the line 2B–2B' in FIG. 2A.
Figure 2A:
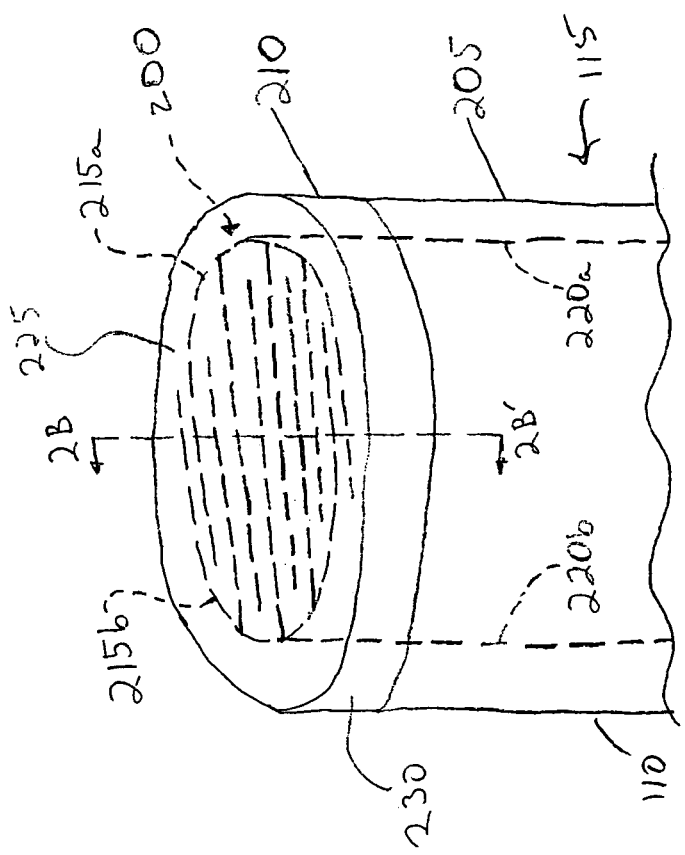
FIG. 2A is a perspective view of a distal portion of the electrosurgical device.
Figure 2D:
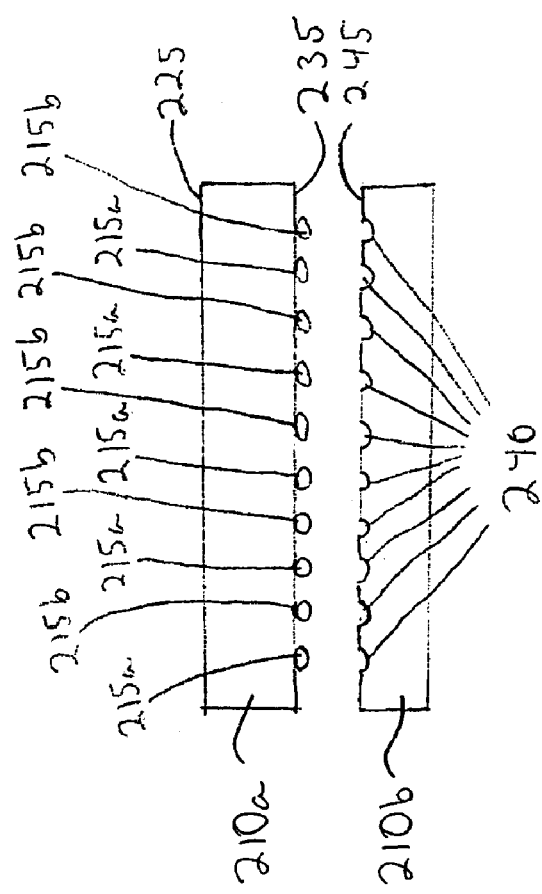
FIG. 2D is a plan view showing the assembly of a disc included as part of the distal portion of the device.
Figure 2C:
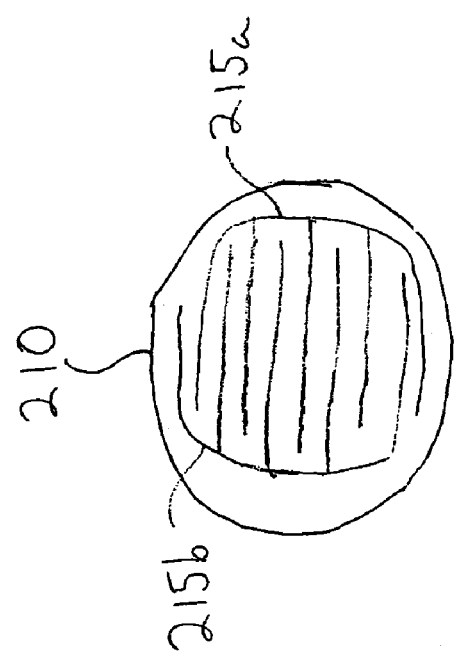
FIG. 2C is a plan view of the distal portion of the device.

Referring to FIGS. 2A–2C, embedded within disc 210 is an RF antenna 200. The RF antenna 200 is constructed from a first plurality of conductive fingers 215a interleaved in a comb-like fashion with a second plurality of conductive fingers 215b such that each one of fingers 215a is adjacent to one of fingers 215b. Fingers 215a and 215b are embedded in disc 210 and are shown in FIG. 2A as dashed lines. However, FIG. 2C illustrates fingers 215a and 215b as solid lines for clarity. Adjacent fingers are equally separated by a distance d, as discussed further below.

The material of disc 210 preferably also has high electrical isolation to limit voltage breakdown between adjacent conductors. This material is preferably resistant to high temperature and the aggressive chemical environment of RF plasmas. Ceramic is an example of a material that is a high dielectric and has good electrical isolation. Some examples of ceramics suitable for use are those made by American Technical Ceramics, One Norden Lane, Huntington Station, N.Y. 11746 with the dielectric designations of CC, EA, or GA.

As shown in FIG. 2A, fingers 215a are connected to a first lead 220a that connects fingers 215a to a first terminal of the RF power generator through power cable 120 and connector 125. Similarly, fingers 215b are connected to a second lead 220b that connects conductors 215b to a second terminal of the RF power generator through power cable 120 and connector 125. Accordingly, fingers 215a receive one polarity of the RF voltage, while fingers 215b receive the opposite polarity. Leads 220a and 220b pass through the hollow portion of shaft 110 to power cable 120.

Referring to FIG. 2D, disc 210 is, e.g., formed from a first section of dielectric material 210a and a second section of dielectric material 210b. First section 210a has a thickness of, e.g., between 5 to 10 mils and second section 210b has a thickness of, e.g., between 20 to 50 mils. Sections 210a and 210b can have the same or different dielectric constants.

First section 210a has tissue treatment surface 225 and a second surface 235 opposite from tissue treatment surface 225. Disposed on second surface 235 are conductive fingers 215a and 215b. Fingers 215a and 215b are disposed on surface 235 using, for example, standard metal deposition and etching techniques.

Second section 210b of dielectric material 210b has a surface 245 with trenches or voids designed to receive conductive fingers 215a and 215b such that fingers 215a and 215b are encapsulated. A bonding technique is used to join surfaces 235 and 245 and to join fingers 215a and 215b to trenches 240 to form a single disc 210 with fingers 215a and 215b embedded therein. Second section 210b provides mechanical strength to disc 210 and electrical isolation between conductive fingers 215a and 215b. Second section 210b can also act to distribute heat from the surface 225.

Referring to FIG. 3, fingers 215a are connected to a first terminal 315 of an RF power generator 305 through lead 220a. Similarly, fingers 215b are connected to a second terminal 310 of RF power generator 305 through second lead 220b.

When connected to RF power generator 305, fingers 215a and 215b radiate RF energy as shown by dashed lines 320, which represent the equipotential lines of the electric field, and solid lines 325, which represent the RF vectors of the electric field. The capacitive impedance of disc 210 distributes the RF energy essentially evenly over surface 225. This electrical impedance is a major component in the RF electrical circuit formed by RF power generator 305, leads 220a and 220b, disc 210 and conductors 215a and 215b. Thus, the surface of disc 210 acts as an RF energy distributing component. As a result, the RF energy density is substantially uniformly spread over surface 225 and is not affected to any significant degree by uneven proximity to the surrounding tissue.

The RF energy is primarily confined to the area in front of surface 225. Consequently, when surface 225 is applied to or near the tissue to be treated, the RF energy is applied primarily to the tissue to be treated, which can, e.g., reduce or eliminate collateral damage.

Different delivery rates of RF energy can be used for various treatments. For example, as described further below, a high RF energy density can be used to ignite a plasma discharge for use in ablating or cutting tissue. In a procedure such as coagulation, on the other hand, the RF energy density is kept low enough to prevent the ignition of a plasma discharge. Coagulation is performed using thermal treatment with a RF current density of up to, for example, about 0.8 A/mm squared. Similarly, an electric field with a low power density can be used to kill cells in a treatment area. This is achieved, e.g., by connecting the probe to a low frequency or a pulsing high frequency, voltage source, such as, a high density pulsed electric field, e.g., a pulsing electric field with a duration of about 1 us to 100 us, a repetition rate from about 10 kHz to 1 Hz, and a voltage field of up to about 200 V/mil (which is equal to 7.9 kV/mm).

Figure 4A:
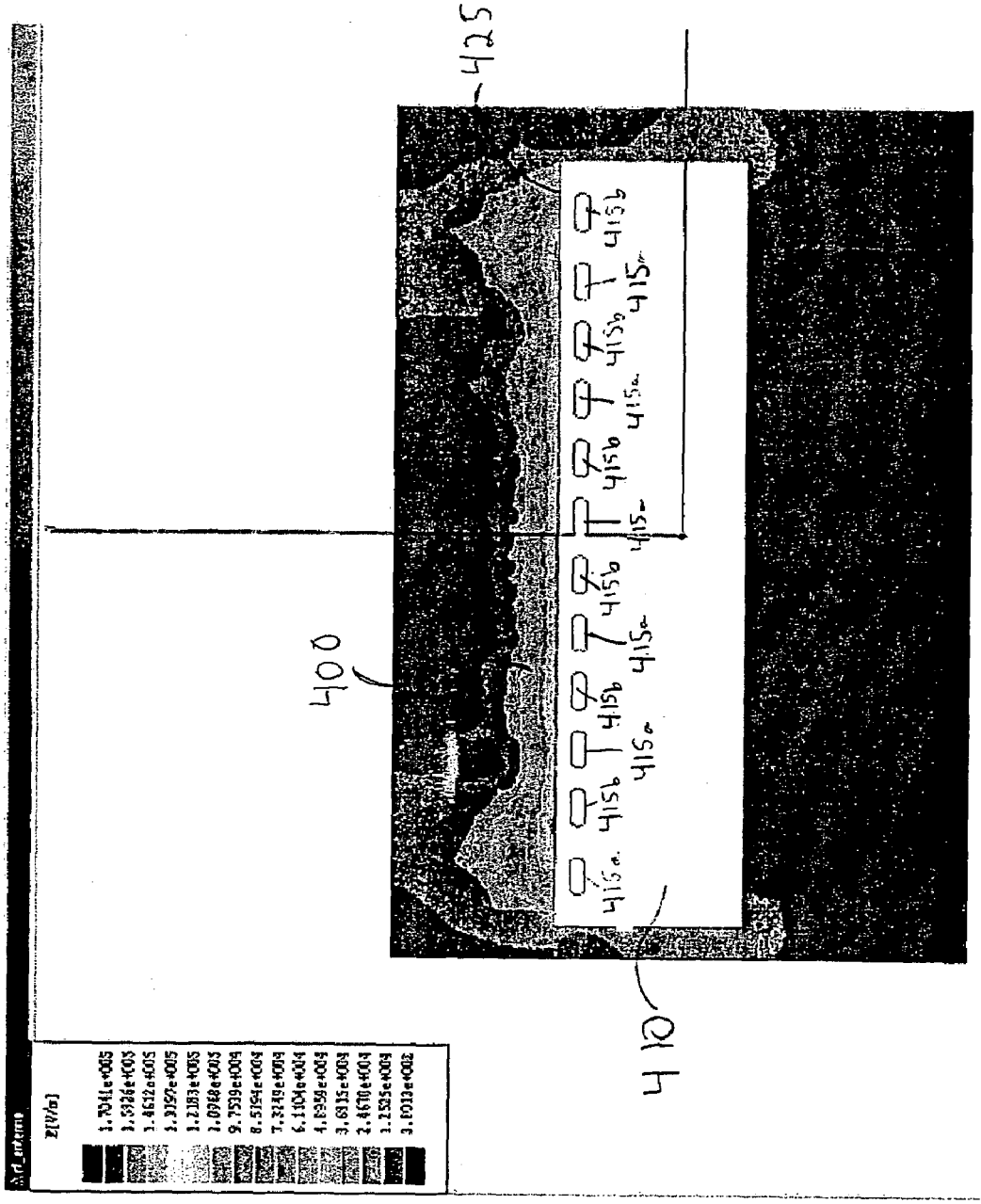
FIGS. 4A and 4B are simulations of the electric field and current density, respectively, at a surface of the distal portion of the device.
Figure 4B:
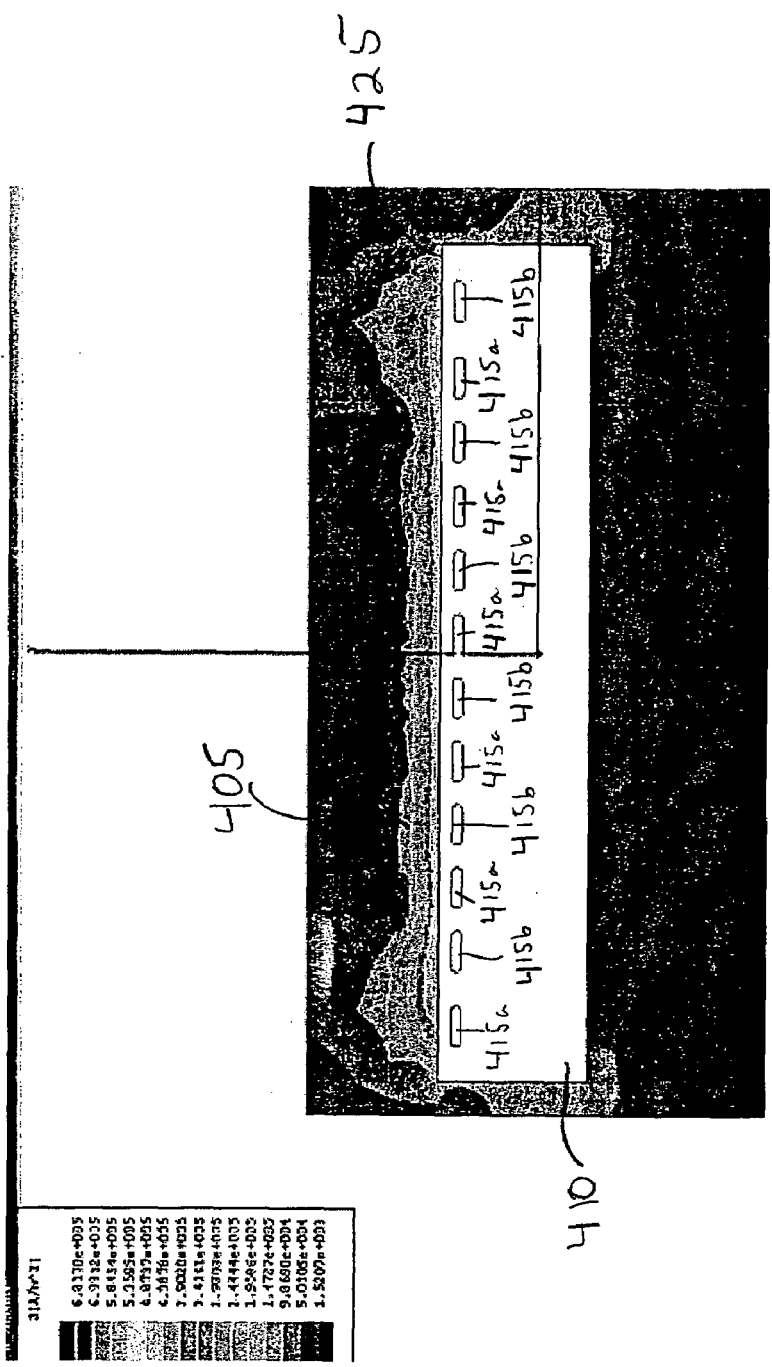

Referring to FIGS. 4A and 4B, a simulation, using finite element analysis software, was conducted to demonstrate that the electric field is located primarily at the treatment surface of the dielectric material. For the simulation, copper with an electrical conductivity of 5.8e+07 Siemens per meter was used for fingers 415a and 415b and ceramic with a dielectric constant of 650 was used for high dielectric material 410. The simulation was a two dimensional simulation, with the height of the ceramic material 210 being 0.065 inches and the width being 0.36 inches. The spacing from surface 425 to conductors 415a and 415b was 0.005 inches. The thickness of conductors 415a and 415b was 0.005 inches and the width of conductors 415a and 415b was 0.0175 inches. The spacing between conductors 415a and 415b was 0.015 inches. The simulation was conducted for a saline environment, using salt water with a dielectric constant of 81 and electrical conductivity of 4 Siemens per meter as the surrounding medium. An RF power source with a voltage magnitude of ±150 V and a frequency of 13 MHz was applied to conductors 415a and 415b, with conductors 415a receiving one polarity and conductors 415b receiving the opposite polarity. As can be seen, electric field 400 and current density 405 radiated outward from surface 425 to a distance of approximately 10 mils and was confined primarily to the area in front of surface 425.

In the simulation, the two end fingers were spaced farther apart from their respective adjacent fingers in an attempt to make the distribution of the electric field and current density more uniform. Because of the boundary conditions at the edges of material 410, for equally spaced fingers 415a and 415b, the distribution of the electric field and current density will be different at the edges of the material than in the central portion. By adjusting the spacing between the fingers at each edge, a more uniform distribution of the RF current and electric field across surface 425 can be achieved.

Unequal spacing can also be used between adjacent conductors so that the RF electric field radiates or extends outward to different distances in different areas of surface 425 or, in other words, an RF field is produced that has different penetration depths in different areas of surface 425. As described, when RF power is applied to fingers 415a and 415b, a high concentration of the RF electric field is created at surface 425. The thickness of this field is a function of the distance d between adjacent fingers of opposite polarity. The further apart conductors of opposite polarity are, the further the electric field extends from surface 425. Thus, the spacing of the conductors can be optimized for specific applications.

Figure 4C:
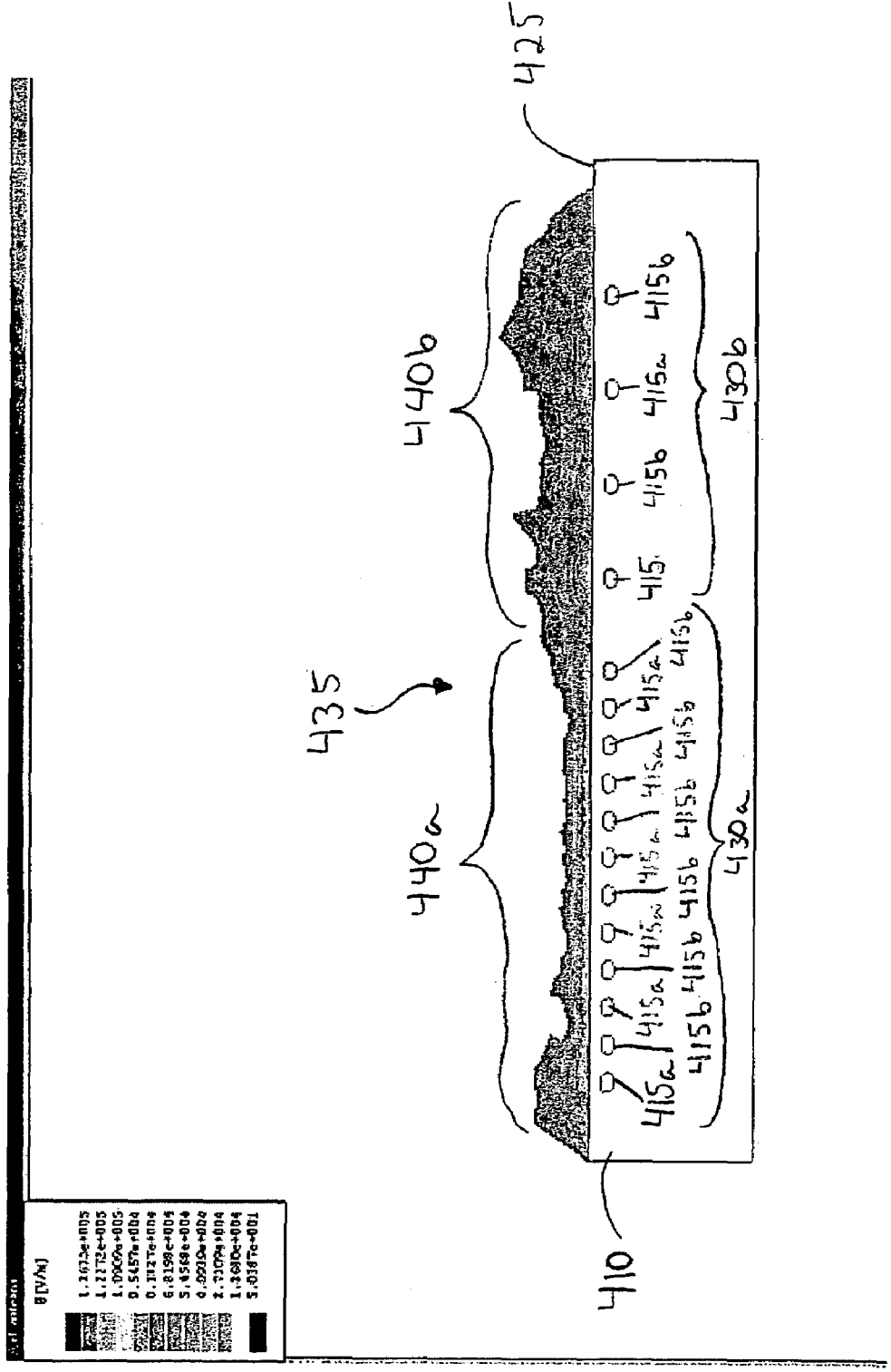
FIGS. 4C and 4D are simulations showing the electric field for alternate configurations of the distal portion.

Referring to FIG. 4C, a simulation was conducted to demonstrate that different penetration depths of the electric field can be achieved with different spacings between adjacent fingers. The width and thickness of the conductors was 7.5 mils and 5 mils, respectively. A first set 430a of fingers 415a and 415b are spaced 7.5 mils apart, while a second set 430b of fingers 415a and 415b are spaced 30 mils apart. The other parameters are the same as those for FIGS. 4A and 4B. As can be seen, the electric field 435 has a first area 440a above the first set 430a of fingers 415a and 415b that extends out from surface 425 a smaller distance than a second area 440b of the electric field 435 above the second set 430b of fingers 415a and 415b. The first area 440a extends approximately 10 mils, while the second area 440b extends approximately 40 mils.

Figure 4D:
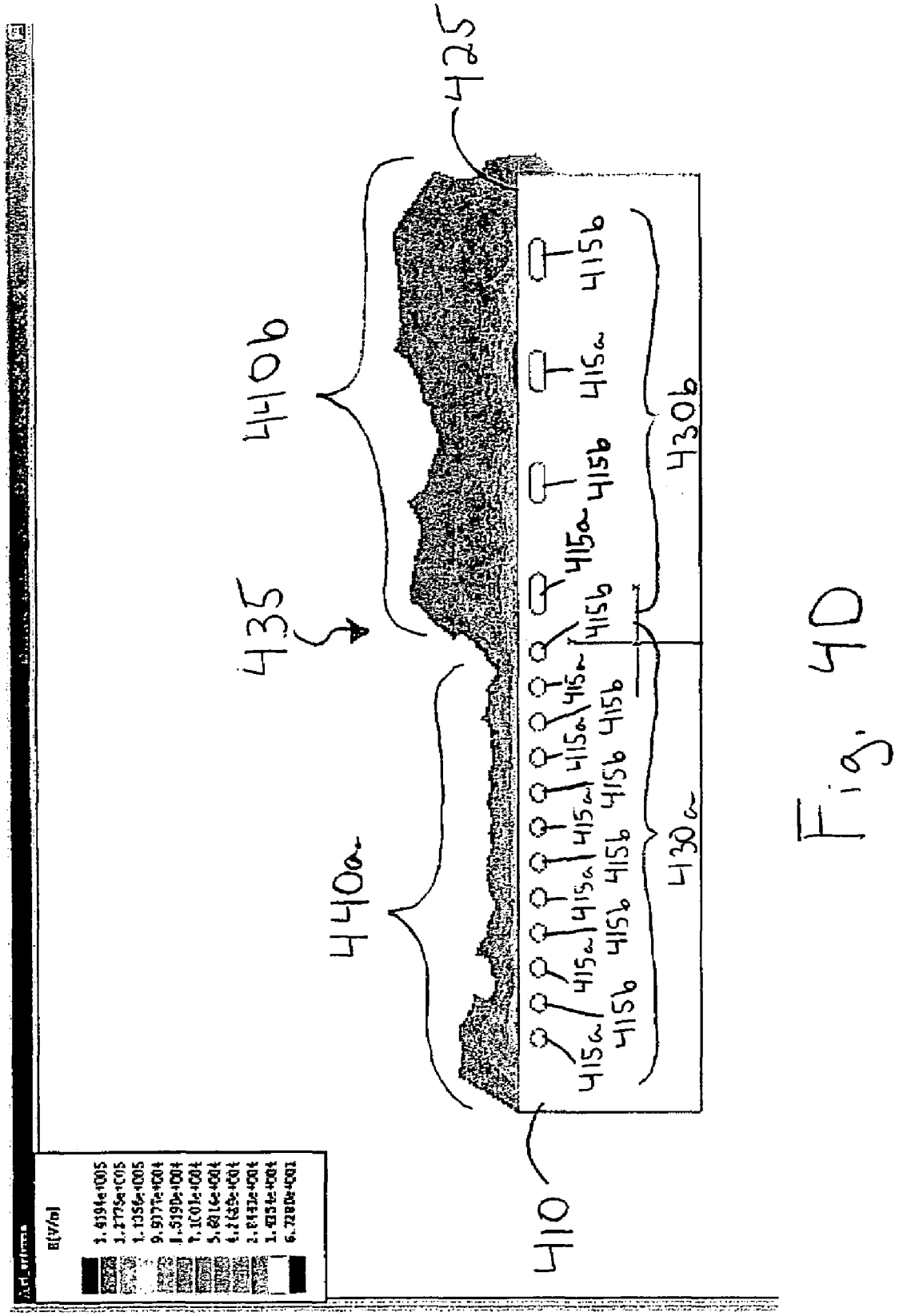

Referring to FIG. 4D, another simulation was performed to demonstrate that the shape of fingers 415a and 415b affects the penetration depth in addition to the spacing between fingers 415a and 415b. The parameters are the same as those for FIG. 4C, except that the width and thickness of the second set 430b of fingers 415a and 415b are 17.5 mils and 5 mils, respectively. As shown, increasing the width of the second set of fingers 430b resulted in the second area 440b of the electric field 435 extending further from surface 425 than first area 440a.

A dielectric barrier discharge (DBD) plasma can be ignited at surface 225 when RF energy is applied to conductors 215a and 215b. This discharge is particularly applicable when the goal is to cut or ablate tissue. The plasma exists primarily in a thin layer over surface 225. As a result, collateral damage due to the plasma is reduced or eliminated.

The current density needed to ignite the discharge plasma is obtained by adjusting the voltage or frequency of the RF power applied for a given thickness and dielectric constant of disc 210. For example, assuming a current density of 0.2 A/mm² is needed to ignite a discharge, then a voltage and frequency of the RF power applied to conductors 215a and 215b equal to 570 V and 5 MHz, respectively, can be used for a thickness of disc 210 equal to 0.125 mm and a dielectric constant of disc 210 equal to 200.

To arrive at this, the following relationship is used:

$$V_{RF} \approx \frac{I_{RF}}{\omega C_{cer}} = \frac{J \cdot A}{\omega C_{cer}}$$

where $V_{RF}$ is the RF voltage, $I_{RF}$ is the RF current, which is equal to the current density J times the area A of the high dielectric material through which the current passes, $\omega$ is the angular frequency of the RF power, and $C_{cer}$ is the capacitance of the high dielectric material.

The capacitance in picofarads is equal to:

$$C_{cer} = 8.5 \cdot 10^{-3} \cdot \varepsilon \cdot \frac{A}{d}$$

where $\varepsilon$ is the dielectric constant of material 210 and d is the thickness of material 210 in millimeters, and A is surface area of material 210 in millimeters squared. Thus, the RF voltage $V_{RF}$ becomes:

$$V_{RF} \approx \frac{J \cdot d}{8.5 \cdot 10^{-3} \cdot \omega \cdot \varepsilon}$$

For a current density of 0.2 A/mm², a dielectric constant of 200, and a thickness of 0.125 mm (which is equivalent to 5 mils):

$$V_{RF} \approx \frac{1.47 \cdot 10^{10}}{\omega}.$$

Choosing a frequency f=5 MHz results in a voltage $V_{RF}$=570V. The frequency or voltage is preferably chosen in view of other parameters such as the dielectric breakdown of disc 210. For example, if disc 210 has a dielectric strength of 150 V/mils, then for a thickness of 5 mils the dielectric material has a breakdown voltage of 750 V. Accordingly, the above parameters could be used without exceeded the breakdown voltage of disc 210.

The particular parameters required to ignite the plasma in a given environment can be determined as a matter of routine experimentation. The frequency of the RF energy can be up to approximately 20 MHz. Theoretically, frequencies higher than 20 MHz can be used, but in practice such high frequencies are difficult to generate and can cause problems such as interference with other electrical devices. Generally, plasma ignition in saline is achieved with approximately a quarter of the RF field strength required for ignition in air.

Figure 5:
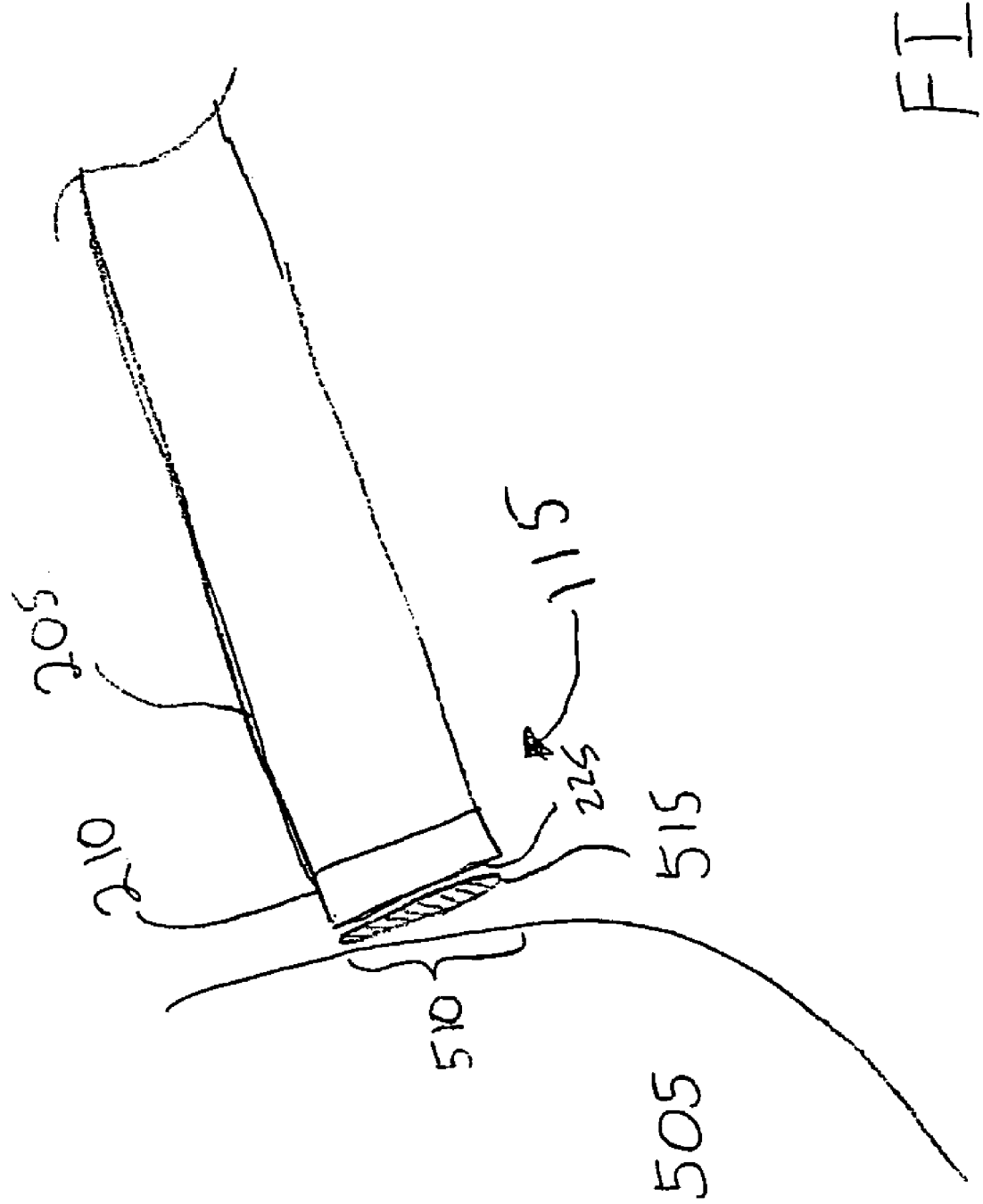
FIG. 5 is a side view showing a use of the electrosurgical device.

Referring to FIG. 5, in use to treat body tissue 505, such as, for example, articular cartilage, surface 225 is placed in contact with a tissue treatment site 510 or near enough to the tissue treatment site 510 that the electric field or plasma discharge region affects the treatment site 510. As a surgeon applies energy to fingers 215a and 215b, RF energy is radiated outward and distributed along surface 225, in a pattern similar to that shown in FIGS. 4A and 4B. In a treatment including, for example, ablation of tissue at tissue treatment site 510, the RF power applied to conductors 215a and 215b is such that a DBD plasma 515 is formed at surface 225. To ablate an area of tissue, distal portion 115 along with plasma 515 is moved along the desired ablation area of tissue.

Other surgical procedures (e.g., coagulation or treatment of skin lesions) is performed without forming a DBD plasma. Rather, the RF electric field distributed across and extending from surface 225, and/or any thermal energy resulting from the electric field, are used to treat the tissue. The heat is dissipated in the treated tissue limiting any collateral damage to the surrounding tissue.

Thus, during use, RF energy is applied to a target tissue with a conductor such that the RF energy is applied without galvanic contact (i.e., without direct electric contact) between the conductor and the target tissue or between the conductor and a conductive medium surrounding the target tissue. In the implementations shown, the RF energy is applied through the dielectric material without the conductors and being in direct electric contact with the tissue and without the conductors being in direct electrical contact with a conductive medium (e.g., saline) surrounding the tissue.

Referring to FIG. 6, for some electrosurgical procedures it is desirable to have the ability to adjust the penetration depth of the RF field. As described above, different spacings between adjacent fingers provide for different penetration depths of the RF field. A switching network 650 is one example of how to adjust the RF electric field's depth of penetration. RF generator 605, disc 610, and fingers 651a and 615b are the same as described in FIGS. 1–3 and fingers 615a and 615b are spaced from one another by a distance $d_1$. Fingers 615a and 615b are connected to RF generator 605 through switching network 650 and three leads 620a, 620b, and 620c. Switching network 650 has two switches, switch 630 and switch 635. When first and second switches 630 and 635 are in a high state (not shown), all of fingers 615a are connected to first terminal 640 of RF generator through both leads 620a and 620b, while all of fingers 615b are connected to second terminal 645 through lead 620c. In this configuration, the distance between adjacent conductors of opposite polarity is $d_1$ and an electric field extends a first length from surface 625 of high dielectric material 610.

When first and second switches 630 and 635 are in a low state (as shown), every other one of fingers 615a are connected to second terminal 645 of RF generator 605 through lead 620b, while the other fingers 615a are connected to first terminal 640. Conductors 615b are not connected to either terminal of RF generator 605. In this configuration, the distance between adjacent conductors of opposite polarity is $d_2$, which is greater than distance $d_1$. As a result, the electric field extends a second length from surface 625, which is farther than the first length.

A number of implementations have been described. Nevertheless, it will be understood that various modifications may be made. For example, other configurations of electrosurgical device 100 have the insulative material of portion 205 covering the side 230 (FIG. 2A) of section 210, while leaving surface 225 exposed. Also, shaft 110 can be made from other materials and with different configurations. For instance, distal portion 115 can have a ninety degree bend such that surface 225 is side-facing. Other bend degrees are also possible such as, for example, sixty degrees, forty-five degrees, or thirty degrees, or the shaft can be flexible with an adjustable angle.

Other dimensions and shapes of disc 210 can be used, depending on the application and the surface area of treatment. Also, while it may be desirable to use a material for disc 210 with high electrical isolation, the material can have some conductivity. For example, a semiconductor material can be used.

Other configurations of disc 210 can also be used. For example, disc 210 has varying dielectric constants along a length and/or diameter. Referring to FIG. 7, for example, conductors 715a and 715b are embedded in disc 710. Disc 710 has three distinct sections, 720, 725, and 730. Each section 720, 725, and 730 is made from a material with a different dielectric constant. Rather than discrete sections, other configurations have gradually varying dielectric constants across a length or diameter.

Further, the second section of dielectric material 210b can be eliminated and other techniques used to insure electrical isolation between conductive fingers 215a and 215b. For example, a coating of glass or other insulating material is applied to surface 235 and conductors 215a and 215b to provide electrical isolation between conductors 215a and 215b. Alternatively, distal portion 115 is configured such that a vacuum exists at the surface 235 of dielectric 210a to provide electrical isolation between conductors 215a and 215b.

Other configurations of the embedded conductors can also be used. Referring to FIG. 8, for example, conductors 715a and 715b are interleaved as concentric circles. Fingers 715a are connected to one terminal of the RF power generator, while fingers 715b are connected to the other terminal.

Moreover, electrosurgical device 100 can have other configurations. For example, electrosurgical device 100 is provided with an internal RF generator, and power cable 120 and connector 125 connect the internal RF generator to AC or DC power. Alternatively, in addition to an internal RF generator, electrosurgical device includes an internal battery to power the RF generator. In this case, power cable 120 and connector 125 are eliminated.

The electrosurgical device can be implemented as a self-coagulating surgical blade. When implemented in this manner, dielectric material 210b is deposited at the surface of a surgical blade for instant coagulation of, e.g., small arteries.

While an electrosurgical device has been described as dimensioned for endoscopic or arthroscopic surgeries, other implementations are dimensioned larger or smaller, depending on the particular application intended. In such applications, the thickness and size of the high dielectric material 210a is adjusted accordingly.

Accordingly, other implementations are within the scope of the following claims.

What is claimed is:

1. An electrosurgical device comprising:
  a high dielectric material having a tissue treatment surface;

a plurality of conductors arranged relative to the high dielectric material such that, in use, the high dielectric material is disposed between the conductors and target tissue;
a power coupling through which power is supplied to the conductors to generate an electric field extending from the tissue treatment surface, the power coupling configured to adjust a penetration depth of the electric field by changing a distance between conductors of opposite polarity.

2. The device of claim 1 wherein:
the conductors comprise a first plurality of conductive fingers and a second plurality of conductive fingers; and
wherein the first plurality of fingers is interleaved with the second plurality of fingers.

3. The device of claim 2 further comprising:
an RF generator; and
wherein the power coupling comprises a switching network coupling the first and second plurality of fingers to the RF generator.

4. The device of claim 3 wherein the switching network has a first state in which the electrical field extends to a first distance from the tissue treatment surface of the high dielectric material and a second state in which the electrical field extends to a second distance from the tissue treatment surface, wherein the second distance is longer than the first distance.

5. The device of claim 2 wherein the first plurality of fingers and the second plurality of fingers are interleaved in a comb-like fashion.

6. The device of claim 1 wherein the at least one conductor and the second conductor each comprise a set of concentric circles, the concentric circles being interleaved.

7. The device of claim 1 further comprising an RE generator coupled to the conductors by the power coupling.

8. The device of claim 7 wherein the RE generator is configured to provide RF power with a voltage and a frequency sufficient to result in a dielectric discharge barrier plasma being formed at a surface of the high dielectric material.

9. The device of claim 8 wherein the RF generator is configured to provide RF power at a frequency up to about 20 MHz.

10. The device of claim 8 wherein the RF generator is configured to provide RF power at a voltage up to about 1500 Vrms.

11. The device of claim 7 wherein the RF generator is configured to provide RF power with a voltage and a frequency sufficient to result in a RF field with current density at a surface of the high dielectric material that is greater than about 0.2 amps per millimeters squared.

12. The device of claim 7 wherein the RF generator is configured to provide RF power with a voltage and a frequency sufficient to result in a RF field with current density at a surface of the high dielectric material that is up to about 1.0 amperes per millimeter squared.

13. The device of claim 7 wherein the RF generator is configured to provide RF power sufficient to result in high density RF currents being formed at a surface of the high dielectric material.

14. The device of claim 7 wherein the RF generator is configured to provide RF power sufficient to result in a high strength RF electrical field being formed at a surface of the high dielectric material.

15. The device of claim 1 wherein the high dielectric material comprises a ceramic material.

16. The device of claim 1 wherein the high dielectric material comprises a material having high electrical isolation.

17. The device of claim 1 wherein the high dielectric material has a dielectric constant greater than approximately 10.

18. The device of claim 17 wherein the high dielectric material has a dielectric constant between about 100 and 1000.

19. The electrosurgical device of claim 1 wherein the power coupling comprises a switching network configured to couple an electrosurgical generator to selective conductors of the plurality of conductors to change the distance between conductors of opposite polarity.

20. A method for performing electrosurgery, the method comprising:
delivering energy to a target tissue through a high dielectric material; and
adjusting a penetration depth of the delivered energy by changing a distance between conductors of opposite polarity.

21. The method of claim 20 wherein the electrosurgery comprises ablating the target tissue.

22. The method of claim 20 wherein delivering the energy further comprises forming a dielectric barrier discharge plasma at a surface of the high dielectric material.

23. The method of claim 22 wherein delivering the energy comprises delivering the energy with a frequency up to about 20 MHz.

24. The method of claim 22 wherein delivering the energy comprises delivering the energy with a RF power density up to about 50 W per millimeter squared.

25. The method of claim 22 wherein the electrosurgery comprises ablating the target tissue.

26. The method of claim 20 wherein delivering the energy further comprises forming high density RF currents at a surface of the high dielectric material.

27. The method of claim 20 wherein delivering the energy further comprises forming a high strength RF electrical field at a surface of the high dielectric material.

28. The method of claim 20 wherein the electrosurgery comprises coagulating the target tissue.

29. The method of claim 20 wherein the electrosurgery comprises treating skin lesions.

30. The method of claim 20 wherein the target tissue is in a non-conductive environment.

31. The method of claim 20 wherein the target tissue is in a conductive environment.

32. The method of claim 20 wherein the target tissue is cartilage.

33. The method of claim 20 wherein the high dielectric material has a dielectric constant greater than approximately 10.

34. The method of claim 33 wherein the high dielectric material has a dielectric constant between about 100 and 1000.

35. An electrosurgical device comprising:
a high dielectric material; and
a plurality of conductors arranged relative to the high dielectric material such that, in use, energy is delivered to a target tissue through the high dielectric material;
a power coupling through which power is supplied to the conductors to generate the energy, the power coupling configured to adjust a penetration depth of the energy by changing a distance between conductors of opposite polarity.

36. A method of performing electrosurgery, the method comprising:

applying RF energy to a target tissue with a conductor, wherein the RF energy is applied without galvanic contact between the conductor and the target tissue or between the conductor and a conductive medium surrounding the target tissue; and adjusting a penetration depth of the applied RF energy by changing a distance between conductors of opposite polarity.

37. An electrosurgical device comprising:

a high dielectric material having a tissue treatment surface;

a first plurality of conductive fingers arranged such that a length of the first plurality of conductive fingers is parallel to the tissue treatment surface;

a second plurality of conductive fingers arranged such that a length of the second plurality of conductive fingers is parallel to the tissue treatment surface, the first plurality of fingers being interleaved with the second plurality of fingers; and wherein the first and second plurality of conductive fingers are arranged relative to the high dielectric material such that, in use, the high dielectric material is disposed between target tissue and the first and second plurality of conductive fingers.

38. The device of claim 37 further comprising:

an RF generator; and a switching network coupling the first and second plurality of fingers to the RF power generator.

39. The device of claim 38 wherein the switching network has a first state in which an RF electrical field extends to a first distance from a tissue treatment surface of the high dielectric material and a second state in which the RF electrical field extends to a second distance from the tissue treatment surface, wherein the second distance is longer than the first distance.

40. The device of claim 37 wherein the first plurality of fingers and the second plurality of fingers are interleaved in a comb-like fashion.

\* \* \* \* \*

UNITED STATES PATENT AND TRADEMARK OFFICE
CERTIFICATE OF CORRECTION

| | | |
|---|---|---|
| PATENT NO. | : 7,182,762 B2 | |
| APPLICATION NO. | : 10/747101 | |
| DATED | : February 27, 2007 | |
| INVENTOR(S) | : Andzrej Bortkiewicz | |

It is certified that error appears in the above-identified patent and that said Letters Patent is hereby corrected as shown below:

Column 4, line 60, change "field with a duration of about 1 us to 100 us, a repetition rate" to --field with a duration of about 1us to 100us, a repetition rate--.

Column 6, line 55, change "Choosing a frequency f=5 MHz results in a voltage" to --Choosing a frequency f=5MHz results in a voltage--; and
      Line 56, change "$V_{RF}$-570V. The frequency or voltage is preferably chosen in" to --$V_{RF}$=570V. The frequency or voltage is preferably chosen in--.

In the claims:
Column 9, line 35, change "7. The device of claim 1 further comprising an RE" to read --7. The device of claim 1 further comprising an RF--; and
      Line 37, change "8. The device of claim 7 wherein the RE generator is" to read --8. The device of claim 7 wherein the RF generator is--.

Signed and Sealed this

Fourteenth Day of October, 2008

JON W. DUDAS
*Director of the United States Patent and Trademark Office*